(12) United States Patent
Baecker et al.

(10) Patent No.: US 10,258,644 B2
(45) Date of Patent: Apr. 16, 2019

(54) SILICON-CONTAINING BIODEGRADABLE MATERIAL FOR ANTI-INFLAMMATORY THERAPY

(71) Applicant: JIANGSU SYNECOUN MEDICAL TECHNOLOGY CO., LTD., Taizhou, Jiangsu Province (CN)

(72) Inventors: Iwer Baecker, Düsseldorf (DE); Christoph Suscheck, Aachen (DE)

(73) Assignee: SIANGSU SYNECOUN MEDICAL TECHNOLOGY CO., LTD., Taizhou (CN)

( * ) Notice: Subject to any disclaimer, the term of this patent is extended or adjusted under 35 U.S.C. 154(b) by 32 days.

(21) Appl. No.: 15/150,919

(22) Filed: May 10, 2016

(65) Prior Publication Data

US 2017/0020915 A1 Jan. 26, 2017

Related U.S. Application Data

(62) Division of application No. 13/579,498, filed as application No. PCT/EP2011/052560 on Feb. 22, 2011, now abandoned.

(30) Foreign Application Priority Data

Feb. 24, 2010 (DE) ........................ 10 2010 008 982

(51) Int. Cl.
| | |
|---|---|
| *A61K 31/765* | (2006.01) |
| *A61K 31/80* | (2006.01) |
| *C04B 35/622* | (2006.01) |
| *C04B 35/624* | (2006.01) |
| *C04B 35/626* | (2006.01) |
| *A61K 33/00* | (2006.01) |

(52) U.S. Cl.
CPC ............ *A61K 31/765* (2013.01); *A61K 31/80* (2013.01); *A61K 33/00* (2013.01); *C04B 35/624* (2013.01); *C04B 35/6224* (2013.01); *C04B 35/6263* (2013.01); *C04B 35/62635* (2013.01); *C04B 35/62685* (2013.01); *C04B 2235/441* (2013.01)

(58) Field of Classification Search
None
See application file for complete search history.

(56) References Cited

U.S. PATENT DOCUMENTS

| | | | |
|---|---|---|---|
| 5,534,509 A | 7/1996 | Konishi et al. | |
| 6,211,393 B1 | 4/2001 | Seguin et al. | |
| 6,335,457 B1 | 1/2002 | Seguin et al. | |
| 8,088,965 B2 | 1/2012 | Thierauf et al. | |
| 2003/0018011 A1 | 1/2003 | Konishi | |
| 2006/0099276 A1 | 5/2006 | Vanden Berghe | |
| 2006/0178268 A1 | 8/2006 | Kros | |
| 2011/0009023 A1 | 1/2011 | Glaubitt et al. | |
| 2011/0123596 A1 | 5/2011 | Baecker et al. | |
| 2011/0183419 A1* | 7/2011 | Glaubitt .............. | C04B 35/6224 435/398 |

FOREIGN PATENT DOCUMENTS

| | | | |
|---|---|---|---|
| DE | 19609551 C1 | 7/1997 | |
| DE | 10 2004 063 599 A1 | 7/2006 | |
| DE | 102007061873 A1 | 7/2008 | |
| EP | 0621038 A1 | 10/1994 | |
| EP | 1262542 A2 | 12/2002 | |
| WO | 96/10575 | 4/1996 | |
| WO | 0142428 A1 | 6/2001 | |
| WO | 2006069567 A2 | 7/2006 | |
| WO | 2008086970 A1 | 7/2008 | |
| WO | WO2008086970 * | 7/2008 | ............. C03B 37/00 |
| WO | 2008148384 A1 | 12/2008 | |
| WO | 2009018356 A1 | 2/2009 | |
| WO | 2009052090 A2 | 4/2009 | |
| WO | 2009077104 A1 | 6/2009 | |
| WO | 2010006708 A1 | 1/2010 | |

OTHER PUBLICATIONS

Kang et al. "Evaluations of Osteogenic and Osteoconductive Properties of a Non-Woven Silica Gel Fabric Made by the Electrospinning Method", Acta Biomaterialia, vol. 5 (2009) pp. 462-469.
Zhang et al. "Vascular Endothelial Growth Factor Promotes Brain Tissue Regeneration With a Novel Biomaterial Polydimethylsiloxane-Tetraethoxysilane", Brain Research, 1132 (2007) pp. 29-35. XP-002631231.
King "Pharmaceutical Preparations and Their Manufacture", Mack Publishing Company, 15th Ed., (1980) p. 1353-1368.
King "Tablets, Capsules, and Pills", Mack Publishing Company, 15th Ed., (1980) pp. 1553-1584.
International Search Report for PCT/EP2011/052560 dated Apr. 15, 2011.

* cited by examiner

*Primary Examiner* — Jake M Vu
(74) *Attorney, Agent, or Firm* — McBee Moore Woodward & Vanik IP, LLC

(57) ABSTRACT

A method for preventing and/or treating a disease associated with increased interleukin-1β and/or interleukin-6 and/or interleukin-8 activity and/or disease, in which a reduction in the activity of interleukin-1β and/or interleukin-6 and/or interleukin-8 is beneficial for healing includes utilizing a silicon-containing, biodegradable material containing a polyhydroxysilicic acid ethyl ester compound, with the proviso that wound defects including chronic diabetic-neuropathic ulcer, chronic leg ulcer, bedsores, secondary-healing infected wounds, non-irritating, primary-healing wounds, ablative lacerations and/or abrasions, are excluded from said disease that is prevented and/or treated with the silicon-containing, biodegradable material.

12 Claims, 7 Drawing Sheets

SILICON-CONTAINING BIODEGRADABLE MATERIAL FOR ANTI-INFLAMMATORY THERAPY

CROSS REFERENCE TO RELATED APPLICATION

This is a divisional application of application Ser. No. 13/579,498, filed on Jan. 16, 2013, which is a national stage application of PCT/EP2011/052560, filed on Feb. 22, 2011, which claims priority of German Application No. 10 2010 008 982.6, filed on Feb. 24, 2010. This application claims the priorities and benefits of all these prior applications and incorporates these prior applications by reference in their entireties.

BACKGROUND OF THE INVENTION

Field of the Invention

The present invention relates to a silicon-containing, biodegradable material for preventing and/or treating diseases that are associated with increased interleukin-1β and/or interleukin-6 and/or interleukin-8 activity or that can be treated by lowering said cytokine activity.

Description of Related Art

Silicon is a trace element, which in bound silicate form is important for humans. Silicon is a building block of the proteins that are responsible for the strength and elasticity of tissues. It is also incorporated in connective tissues, bone, skin, hair, nails and blood vessels. Moreover, silicon strengthens the body's defence system, the so-called immune system, and promotes wound healing. Silicon deficiency leads to growth disorders, loss of bone stability with increased risk of osteoporosis, as well as premature hair loss, brittle nails and changes in the skin. Possible changes in the skin are increased wrinkle formation, dryness, desquamation, increased cornification, pruritus, thickening and painful cracking of the skin due to reduced elasticity. Moreover, the body's defence system, the so-called immune system, is weakened by silicon deficiency and there is increased susceptibility to infections.

US2006/0178268A1 describes an aqueous solution consisting of non-colloidal silicic acid and boric acid for treating diseases of bone, cartilage, skin, arteries, connective tissues, joints, hair, nails, and skin, as well as osteoporosis, rheumatic diseases, arteriosclerosis, arthritis, cardiovascular diseases, allergic diseases and degenerative diseases.

US2006/0099276A1 discloses a method of producing a silica derivative by hydrolysis of a silicone compound to oligomers with simultaneous presence of a quaternary ammonium compound, an amino acid or a source of amino acid or combinations thereof. The silica extrudate can be used as pharmaceuticals for treating infections, diseases of the nails, hair, skin, teeth, collagen, connective tissues, and bone, osteopenia, for cell formation for degenerative (ageing) processes.

U.S. Pat. No. 6,335,457B 1 discloses a solid substance in which silicic acid is complexed with a polypeptide. This patent also discloses therapeutically usable mixtures comprising this solid substance.

WO2009/018356A1 relates to a mixture comprising a sodium phosphate compound, an ammonium compound and a silicate for preventing or treating diseases such as prostate cancer, colorectal cancer, lung cancer, breast cancer, liver cancer, neuronal cancer, bone cancer, HIV syndrome, rheumatoid arthritis, multiple sclerosis, Epstein-Barr virus, fibromyalgia, chronic fatigue syndrome, diabetes, Bechet's syndrome, irritable bowel syndrome, Crohn's disease, decubitus, trophic ulcers, immune system weakened by radiotherapy or chemotherapy, haematomas or combinations thereof.

WO2009/052090A2 describes a method for treating inflammatory diseases, autoimmune diseases, bacterial or viral infections and cancer, using a composition that contains silicate.

US2003/0018011A1 relates to a pharmaceutical composition with a fatty acid and a water-soluble silicate polymer as anti-allergic or as anti-inflammatory agent.

U.S. Pat. No. 5,534,509 relates to a pharmaceutical composition containing a water-soluble silicate polymer as active agent with a saccharide or sugar alcohol as inert carrier for treating allergies, inflammations, pain or for improving the peripheral blood circulation or paraesthesia.

DE19609551C1 describes the production of bioabsorbable (continuous) fibres based on polyhydroxysilicic acid ethyl ester. The fibres are used as reinforcing fibres for biodegradable and/or bioabsorbable (implant) materials. The fibres can also be used for the production of biodegradable composites.

WO01/42428A1 describes a method of producing a skin implant, wherein skin cells are applied on the surface of a nutrient solution and are grown with the aid of a surface element consisting of the fibres described in DE19609551C1.

EP1262542A2 relates to a method of in-vitro production of cells, tissues and organs, wherein a fibre matrix is used as cell support and/or directing structure according to DE19609551C1.

WO2006/069567 A2 relates to a multilayer dressing in which a fibre matrix according to DE19609551C1 is also used in one layer. The multilayer dressing can be used for treating wound defects, such as chronic diabetic-neuropathic ulcer, chronic leg ulcer, bedsores, secondary-healing infected wounds, non-irritating, primary-healing wounds, such as in particular ablative lacerations or abrasions.

WO2008/086970A1, WO2008148384A1, PCT/EP2008/010412 and PCT/EP2009/004806 describe, among other things, the production of other polyhydroxysilicic acid ethyl ester compounds usable according to the invention. The compounds are described generally for use as bioabsorbable materials in human medicine, medical engineering, filter technology, biotechnology or the insulating materials industry. It is also mentioned that the materials can be used advantageously in the area of wound treatment and wound healing. Fibres can be used for example as surgical suture material or as reinforcing fibres. Nonwoven materials can be used in the care of superficial wounds, in the filtration of body fluids (e.g. blood) or as a culture aid in the area of bioreactors.

It is not disclosed in the prior art that the aforementioned biodegradable polyhydroxysilicic acid ethyl ester compounds (e.g. in the form of a fibre or a nonwoven fabric) can be used for preventing and/or treating diseases that are associated with increased interleukin-1β and/or interleukin-6 and/or interleukin-8 activity or that can be treated by lowering said cytokine activity. The use of the polyhydroxysilicic acid ethyl ester compounds for wound treatment and wound healing is certainly described in the aforementioned documents and it is known that wound healing is associated with pro- or anti-inflammatory processes, but the prior art does not describe generally using the aforementioned biodegradable polyhydroxysilicic acid ethyl ester compounds prophylactically and/or therapeutically in particular for inflammatory and/or autoimmune diseases.

SUMMARY

The present invention therefore relates to a silicon-containing, biodegradable material for preventing and/or treating diseases that are associated with increased interleukin-1β and/or interleukin-6 and/or interleukin-8 activity and/or diseases in which a reduction in the activity of interleukin-1β and/or interleukin-6 and/or interleukin-8 is beneficial for the healing process, wherein the silicon-containing, biodegradable material is a polyhydroxysilicic acid ethyl ester compound, with the proviso that wound defects, such as chronic diabetic-neuropathic ulcer, chronic leg ulcer, bedsores, secondary-healing infected wounds, non-irritating, primary-healing wounds, such as in particular ablative lacerations or abrasions, are excluded. The invention also comprises the use of a silicon-containing, biodegradable polyhydroxysilicic acid ethyl ester compound for producing a medicinal product for preventing and/or treating diseases that are associated with increased interleukin-1β and/or interleukin-6 and/or interleukin 8 activity and/or diseases in which a reduction in the activity of interleukin-1β and/or interleukin-6 and/or interleukin-8 is beneficial for the healing process, with the proviso that wound defects, such as chronic diabetic-neuropathic ulcer, chronic leg ulcer, bedsores, secondary-healing infected wounds, non-irritating, primary-healing wounds, such as in particular ablative lacerations or abrasions, are excluded.

DETAILED DESCRIPTION OF A PREFERRED EMBODIMENT

Figure 1A:
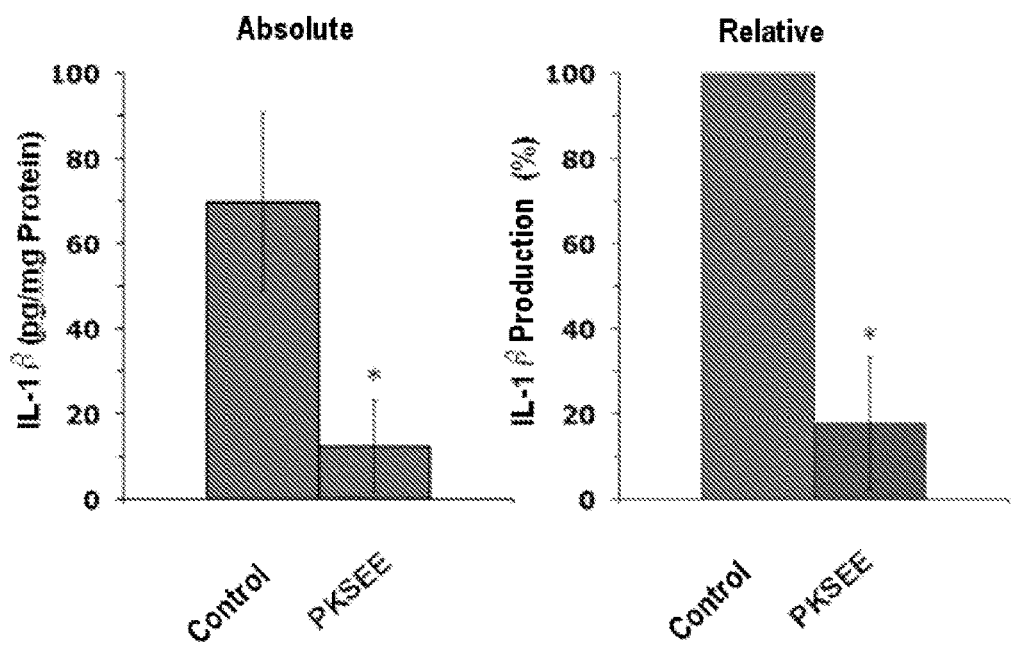
FIGS. 1a-7b depict embodiments of the present invention as described herein.

The invention does not include those uses of the material according to the invention that are described in the following patent documents DE19609551C1, WO01/42428A1, EP1262542A2, WO2006/069567A2, WO2008/086970A1, WO2008148384A1, PCT/EP2008/010412 and PCT/EP2009/004806 and are related to the present invention. The use of a polyhydroxysilicic acid ethyl ester fibre nonwoven material as a component of a multilayer dressing was described in WO2006/069567 A2 for treating wound defects, such as chronic diabetic-neuropathic ulcer, chronic leg ulcer, bedsores, secondary-healing infected wounds, non-irritating, primary-healing wounds, such as in particular ablative lacerations or abrasions. EP1262542A2 describes various tissue-engineering uses of polyhydroxysilicic acid ethyl ester compounds according to the invention. The term "tissue-engineering uses" according to the present invention is directed at the products, methods and uses described in EP1262542A2. Therefore the invention does not include the tissue-engineering uses of the silicon-containing, biodegradable material according to the invention discussed in EP1262542A2, if these are connected with the object of the present invention.

The term "polyhydroxysilicic acid ethyl ester compound" describes all compounds according to the invention of the general formula $H[OSi_8O_{12}(OH)_x(OC_2H_5)_{6-x}]_nOH$, in which x stands for 2 to 5 and n>1 (polymer).

The silicon-containing, biodegradable material according to the invention is preferably a material in the form of a fibre, a fibre matrix, as powder, as monolith and/or as coating. This silicon-containing, biodegradable material can be produced according to the invention as described below:
a) at least one hydrolysis-condensation reaction of tetraethoxysilane,
b) evaporation for producing a single-phase solution preferably with simultaneous gentle mixing of the reaction system,
c) cooling of the single-phase solution and
d) maturation for production of a silica sol material,
e) drawing of threads from the silica sol material to generate a fibre or a fibre matrix and/or drying and in particular spray drying or freeze-drying of the silica sol material to generate a powder and optionally dissolving the powder in a solvent to generate a liquid formulation and/or coating an object that is to be coated with the silicon-containing, biodegradable material, with the silica sol material, and/or casting the silica sol material in a mould to generate a monolith.

Preferably, according to the invention, the silicon-containing, biodegradable material of the invention is in the form of fibre, fibre matrix (nonwoven fabric), powder, liquid formulation and/or coating.

In another embodiment of the invention, the silicon-containing, biodegradable material according to the invention is produced as described above, wherein the tetraethoxysilane is acid-catalysed in step a) at an initial pH from 0 to ≤7, optionally in the presence of a water-soluble solvent, preferably ethanol, at a temperature from 0° C. to 80° C., and in step b) evaporation is carried out to a single-phase solution with a viscosity in the range from 0.5 to 2 Pa·s at a shear rate of 10 s$^{-1}$ at 4° C.

In another embodiment of the invention, the silicon-containing, biodegradable material is produced as described above, wherein the acid catalysis is carried out in step a) with aqueous solution of nitric acid in a molar ratio to the Si compound in the range 1:1.7 to 1:1.9, preferably in the range from 1:1.7 to 1:1.8. The hydrolysis-condensation reaction in step a) preferably takes place at a temperature from 20 to 60° C., preferably 20 to 50° C. over a period of at least one hour. Preferably the hydrolysis-condensation reaction in step a) proceeds for a period of several hours, for example 8 h or 16 h. However, this reaction can also be carried out for a period of 4 weeks. In a preferred embodiment of the invention, step (b) is carried out in a closed apparatus, in which mixing is possible (preferably rotary evaporator or stirred vessel) with simultaneous removal of the solvent (water, ethanol) by evaporation at a pressure from 1 to 1013 mbar, preferably at a pressure of <600 mbar, optionally with continuous feed of a chemically inert carrier gas for lowering the partial pressure of the evaporating components of 1-8 m$^3$/h (preferably at 2.5 to 4.5 m$^3$/h), a reaction temperature from 30° C. to 90° C., preferably 60 to 75° C., more preferably at 60 to 70° C. and preferably with gentle stirring of the reaction system at up to 80 rev/min (preferably at 20 rev/min to 80 rev/min) up to a viscosity of the mixture of 0.5 to 30 Pa·s at a shear rate of 10 s$^{-1}$ at 4° C., preferably 0.5 to 2 Pa·s at a shear rate of 10 s$^{-1}$ at 4° C., especially preferably approx. 1 Pa·s (measurement at 4° C., shear rate 10 s$^{-1}$). In another embodiment of the invention, the silicon-containing, biodegradable material is cooled in step c) preferably to 2° C. to 4° C. Maturation (step d) preferably also takes place at this low temperature. Maturation may take several hours or days, up to about 3 to 4 weeks. The maturation process in step d) is preferably carried out up to a viscosity of the sol from 30 to 100 Pa·s at a shear rate of 10 s$^{-1}$ at 4° C. and a loss factor from 2 to 5 (at 4° C., 10 l/s, 1% deformation).

The drawing of threads from the silica sol material in step e) is preferably carried out by a spinning process. Said spinning step can be carried out in usual conditions, as described for example in DE 196 09 551 C1 and DE 10 2004 063 599 A1.

The drying of the silica sol material for generating powder is preferably carried out by spray drying or freeze-drying. A powder can also be obtained by comminution and grinding of monoliths or also of fibres according to the invention. To generate a liquid formulation, the powder is dissolved in a solvent. Suitable solvents can be aqueous or oily, depending on the application (e.g. solution for injection or suspensions).

An object that is to be coated with the silicon-containing, biodegradable material is preferably coated with the silica sol material by immersing the article to be coated in the silica sol, by sprinkling or by spin-coating or spraying of the silica sol.

The silica sol material according to step d) can also—to generate a monolith—be cast in a mould and then dried.

Further, more-specific information regarding production of the silicon-containing, biodegradable materials according to the invention can be found in DE19609551C1, WO01/42428A1, EP1262542A2, WO2006/069567A2, WO2008/086970A1, WO2008148384A1, PCT/EP2008/010412 and PCT/EP2009/004806.

In the sense of the present invention, the expression "biodegradable" denotes the property of the polyhydroxysilicic acid ethyl ester compound according to the invention to be degraded, when the material is exposed to conditions that are typical of those prevailing during tissue regeneration (for example of a wound). The polyhydroxysilicic acid ethyl ester compound according to the invention is "biologically degradable" or "biodegradable" in the sense of the invention in particular when it dissolves completely after 48 hours, preferably 36 hours and especially preferably after 24 hours in a 0.05 M Tris pH 7.4 buffer solution (Fluka 93371) thermostatically controlled at 37° C.

Cytokines and chemokines regulate inflammations and reactions to infections, injuries and cancer. Whereas some cytokines intensify reactions to exogenous and endogenous material, other cytokines reduce inflammations and thus promote healing. The expression and production of almost all proinflammatory cytokines is controlled in the context of inflammatory reactions via signalling pathways, which are regulated by the NFκKB transcription factor. NFκB is therefore also the central regulatory molecule in the induction of interleukin-1β, interleukin-6 and interleukin-8. Interleukin-1β, interleukin-6 and interleukin-8 are inflammation intensifying or inflammation initiating cytokines, which are associated with fever, inflammations, tissue destruction and in some cases shock and death. Reducing the biological activity of IL-1β and/or IL-6 and/or IL-8 is therefore the aim of various therapeutic measures and is applied successfully in a large number of inflammatory diseases.

The term "diseases that are associated with increased interleukin-1β and/or interleukin-6 and/or interleukin-8 activity and/or diseases in which a decrease in activity of interleukin-1β and/or interleukin-6 and/or interleukin-8 is beneficial for the healing process" preferably describes diseases comprising:

autoimmune diseases, allergies, enteritis, colitis, gastritis, arthritis, myocarditis, dermatitis, otitis, pneumonitis, shock lung, blood clotting disorders, inflammatory bone and joint diseases, rheumatoid arthritis, sepsis, septic shock, post-transplantation sequelae, acute and chronic inflammations, inflammatory bowel disease, graft-versus-host disease, shock, stroke, acute respiratory syndrome (ARDS), psoriasis, restenosis, AIDS, cachexia, cerebrocranial trauma, allergy, parasitic infection, allergic rhinitis, allergic asthma, atopic dermatitis, multiple sclerosis, systemic lupus erythematosus, graft-versus-host disease, transplant rejection, asthma and chronic obstructive pulmonary disease, chronic gastritis, acute and chronic inflammations of the skin, psoriasis, skin allergies, parasitic skin infection, atopic dermatitis especially neurodermatitis, dermatomyositis, pemphigus vulgaris and/or other local and systemic infections and/or acute and chronic inflammatory situations.

The autoimmune diseases include m particular the following diseases: alopecia areata, antiphospholipid syndrome, amyotrophic lateral sclerosis, autoimmune polyendocrinopathycandidiasis-ectodermal dystrophy (polyendocrine autoimmune disease), arteritis temporalis, atherosclerosis, autoimmune enteropathy, CREST syndrome, Crohn's disease, dermatomyositis, dermatitis herpetiformis Duhring, diabetes mellitus type 1, epidermolysis bullosa acquisita, fibromyalgia, chronic autoimmune gastritis, Goodpasture syndrome, Guillain-Barre syndrome, Hashimoto thyroiditis, PANDAS, hyperthyroidism, idiopathic thrombocytopenic purpura, connective tissue disease, juvenile rheumatoid arthritis, coronary heart diseases, craniomandibular dysfunction, cryoglobulinaemia, cold agglutinin disease, lichen sclerosus, linear IgA dermatosis, Lyme arthritis, lupus erythematosus, mixed collagenosis, Addison's disease, Basedow disease, myasthenia gravis, narcolepsy, pemphigus vulgaris, pernicious anaemia (Biermer disease), Werlhof disease, myasthenia gravis, polymyositis, primary biliary cirrhosis, polymyalgia rheumatica, rheumatoid arthritis, Sjogren syndrome, scleroderma, stiff-man syndrome, sympathetic ophthalmia, giant cell arteritis, ulcerative colitis, vasculitis, Wegener granulomatosis, Bechterew disease, autoimmune hepatitis, bullous pemphigoid, pemphigus seborrheicus, polyangiitis, polyneuropathy, Reiter syndrome, rheumatic fever, Churg-Strauss syndrome, sinusitis, sarcoidosis, Takayasu arteritis, toxoplasmosis, glomerulonephritis, Hashimoto thyroiditis, Adamantiades-Beheet disease, relapsing polychondritis, panchondritis, systematized chondromalacia, polychondritis atropicans, polyendocrine autoimmune insufficiency, Schonlein-Henoch purpura (purpura anaphylactoides, vasculitis allergica), vitiligo, coeliac disease, autoimmune nephritides and vasculitides and/or autoimmune leukaemias.

Diseases that are preferably treated with the compound according to the invention are acute and chronic inflammations of the skin, psoriasis, skin allergies, parasitic skin infection, atopic dermatitis in particular neurodermatitis, dermatomyositis and/or pemphigus vulgaris.

The suitable dosage of the polyhydroxysilicic acid ethyl ester compound is generally in total between 0.001 and 100 mg/kg body weight per day and is administered as a single dose or in multiple doses. A dosage between 0.01 and 25 mg/kg, more preferably 0.1 to 5 mg/kg per day is preferably used. However, the biodegradable properties of the polyhydroxysilicic acid ethyl ester compounds also mean that the compounds can be applied in higher dosages and for example degrade inside the body, e.g. subcutaneously as depot in the form of a monolith, over an extended period.

The material according to the invention or a precursor thereof (such as for example the silica sol material described above in step d)) can be processed with the carrier substances, fillers, disintegration modifiers, binders, lubricants, absorbents, diluents, flavour correctants, colorants etc. that are usual in pharmaceutics, and transformed into the desired dosage form. Reference may be made to Remington's Pharmaceutical Science, 15th ed. Mack Publishing Company, East Pennsylvania (1980).

The material according to the invention can be administered in a suitable dosage form by the oral, mucosal (for example sublingual, buccal, rectal, nasal or vaginal), parenteral (for example subcutaneous, intramuscular, by bolus injection, intraarterial, intravenous), transdermal route or locally (for example direct application on the skin or topical application on an exposed organ or a wound).

In particular, tablets, coated tablets, film-coated tablets, capsules, pills, powders, granules, pastilles, suspensions, emulsions or solutions may come into consideration for oral application.

Tablets, coated tablets, capsules etc. can be obtained for example as described above by casting the silica sol material obtained in step d) in a tablet-shaped or capsule-shaped mould to generate a monolith. However, the tablets and capsules can also be produced by means of the material according to the invention described above in the form of a powder, by the usual methods. Known excipients, for example inert diluents such as dextrose, sugar, sorbitol, mannitol, polyvinylpyrrolidone, disintegrants such as maize starch or alginic acid, binders such as starch or gelatin, lubricants such as magnesium stearate or talc and/or agents for achieving a depot effect such as carboxypolymethylene, carboxymethylcellulose, cellulose acetate phthalate or polyvinyl acetate can be added to the material according to the invention or a precursor thereof. Tablets can also consist of several layers. Capsules containing the materials according to the invention can for example be produced by mixing the materials according to the invention or a precursor thereof with an inert carrier such as lactose or sorbitol and encapsulating them in gelatin capsules. Correspondingly, coated tablets can be produced by coating cores, produced similarly to the tablets, with agents usually employed in tablet coatings, for example polyvinylpyrrolidone or shellac, gum arabic, talc, titanium dioxide or sugar. The shell of the coated tablets can also consist of several layers, wherein the excipients mentioned above for tablets can be used.

For parenteral application, injection and infusion preparations are possible. For intraarticular injection, correspondingly prepared crystal suspensions can be used. For intramuscular injection, liquid formulations such as aqueous and oily solutions for injection or suspensions and corresponding depot preparations find application. For rectal administration, the materials according to the invention can be used in the form of suppositories, capsules, solutions (e.g. in the form of enemas) and ointments both for systemic and for local therapy. Furthermore, agents for vaginal use may also be mentioned as preparations. Liquid formulations such as solutions for injection or suspensions can be obtained for example by adding suitable aqueous or oily solvents to the material according to the invention described above in the form of a powder. Other types of production are known by a person skilled in the art. Solutions or suspensions of the material according to the invention can additionally contain taste improving agents such as saccharin, cyclamate or sugar and for example flavourings such as vanillin or orange extract. They can in addition contain suspending aids such as sodium carboxymethylcellulose or preservatives such as p-hydroxybenzoate. Suitable suppositories can be produced for example by mixing the appropriate carriers such as neutral fats or polyethylene glycol or derivatives thereof.

Patches are possible for transdermal application, or formulations as gels, ointments, fatty ointments, creams, pastes, powder, milk and tinctures for topical application. Plasters preferably consist of fibres or a fibre matrix (nonwoven fabric) made from the materials according to the invention, as described in the prior art.

In another embodiment of the invention, the material according to the invention or a precursor thereof can be coated by a coating process, for example by dipping an object or article to be coated in the silica sol material described above in step d), by sprinkling or by spin-coating or spraying said silica sol material. For example, the silica sol material according to the invention can be coated on plasters or dressings.

The aforementioned dosage forms can also contain other active pharmaceutical ingredients, which can be added during the production process.

1. Production of a Fibre Matrix According to the Invention from Polyhydroxysilicic Acid Ethyl Ester As educt for the hydrolysis-condensation reaction, 1124.98 g TEOS (tetraethoxysilane) was put in a stirred vessel. 313.60 g EtOH was added as solvent. The mixture is stirred. Separately, 1 n $HNO_3$ (55.62 g) was diluted with $H_2O$ (120.76 g) and was added to the TEOS-ethanol mixture. The mixture was stirred for 18 hours.

The mixture obtained by this step was then evaporated at temperatures of 62° C. with feed of a carrier stream and stirring (60 rev/min) to a dynamic viscosity (shear rate 10 s−1 at 4° C.) of 1 Pa·s.

The solution was then matured in a closed polypropylene maturation beaker at rest and upright at a temperature of 4° C. to a dynamic viscosity of approx. 55 Pa·s (shear rate 10 s−1 at 4° C.) and a loss factor of 3.0.

The sol resulting from maturation was then spun into fibre. The production of the fibres was carried out in a usual spinning apparatus. For this, the spinning material was filled in a pressure cylinder cooled to −15° C. The spinning material was forced under pressure through the nozzles. Depending on the local temperature and therefore the viscosity of the spinning material, the emerging spun threads had a diameter of approx. 50 μm. The free-flowing, honey-like material fell under its own weight into a spinning shaft with length of 2 m located under the pressure cylinder. Temperature and humidity were controlled in the spinning shaft. The temperature was 25° C. and the air humidity was 19%. As the threads came onto the changing table, they practically retained their cylindrical shape, but were still flowable, so that at their contact surfaces they stuck together as bundles of fibres (nonwovens).

2. Constitutive and Induced Interleukin-1β Synthesis in Keratinocytes

To determine the effect of the fibre matrix produced in example 1 from polyhydroxysilicic acid ethyl ester (abbreviated as PKSEE in the figures) on the constitutive interleukin-1β synthesis in keratinocytes, 6-well cell culture plates were used with 200 000 keratinocytes and 3 ml growth medium in each well. The cell culture plates were then fitted with suitable plastic hangers. In the case of testing of the polyhydroxysilicic acid ethyl ester compound, in each case 1 $cm^2$ of a polyhydroxysilicic acid ethyl ester fibre matrix was inserted in the hangers and covered with 1 ml of medium. In controls, the hangers were supplemented with 1 ml of medium. The contents of the plastic hangers are separated by a membrane from the cell culture medium. Owing to the permeability of the membrane, however, exchange of dissolved substances is possible between the contents of the hangers and the cell culture medium. The culture plates were cultivated for 2 to 4 days. The absolute and relative amount of interleukin-1β in the cell culture supernatant was then determined with an ELISA assay [human IL-1 beta ELISA kit from R&D Systems]. FIG. 1a shows a marked and significant reduction in constitutive interleukin-1β synthesis after 72 hours of culture [Student's t-test].

Figure 1B:
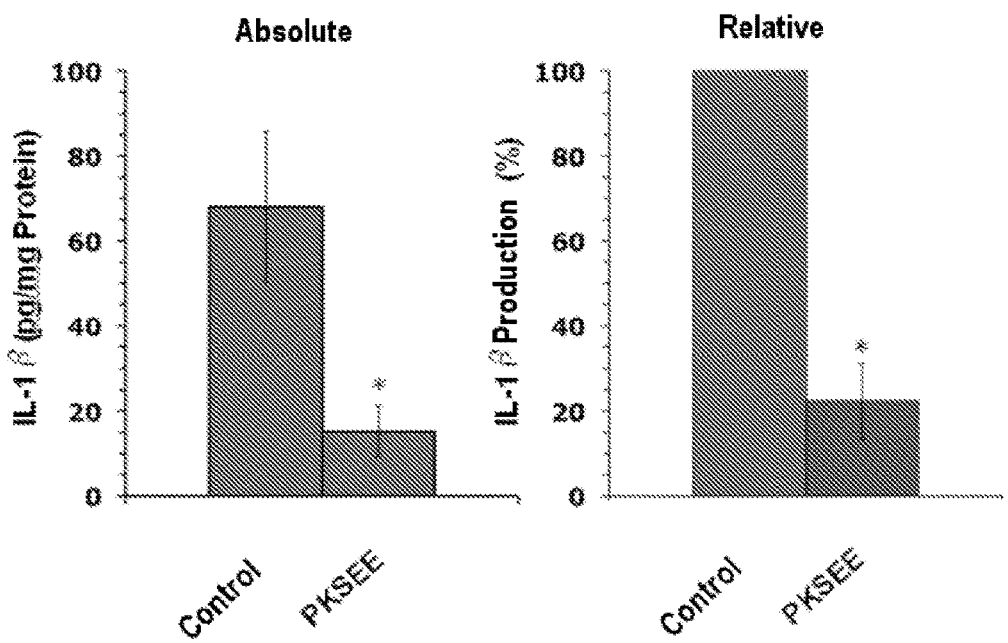

Another test was carried out similarly, the only difference being that the keratinocytes were activated at the beginning for 24 hours by adding IL-β [500 units/ml]. Then, by washing several times, the exogenously added IL-1β was removed from the cultures and the cultures were cultured for a further 24 hours in the normal growth medium. FIG. 1b shows, in comparison with untreated cultures, a marked and significant [Student's t-test] reduction in induced interleukin 1 B synthesis of the keratinocyte cultures treated with the material according to the invention.

Figure 2A:
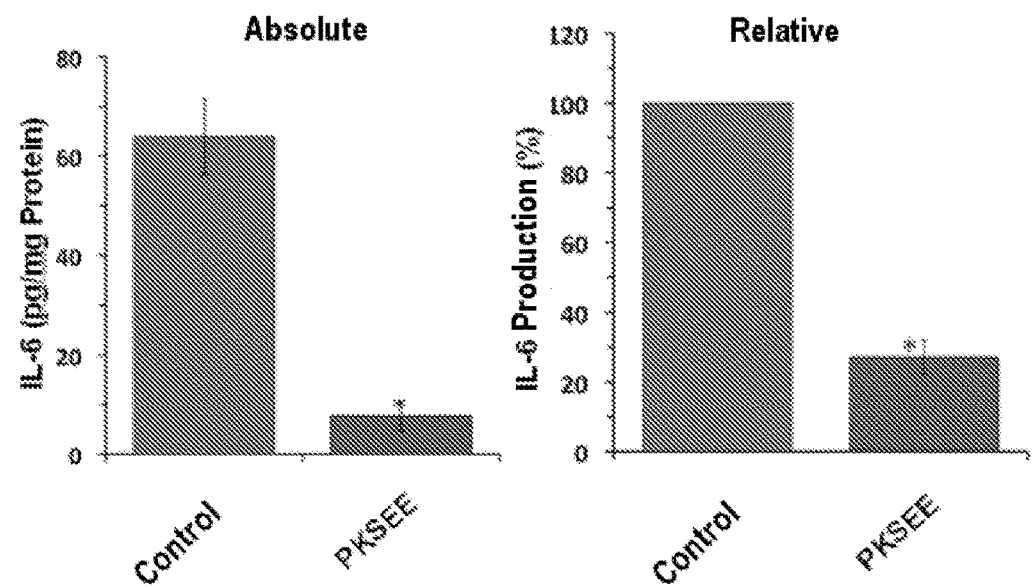

3. Constitutive and Induced Interleukin-6 Synthesis in Keratinocytes, Endothelial Cells and Fibroblasts The same tests as described in Ex. 2 were carried out, except that instead of interleukin-1β, the absolute and relative amount of interleukin-6 was determined in the cell culture supernatant with an ELISA assay [Human IL-6 ELISA kit from R&D Systems]. FIG. 2a shows a marked and significant [Student's t-test] reduction in constitutive interleukin 6 synthesis in keratinocytes after 72 hours of culture.

Figure 2B:
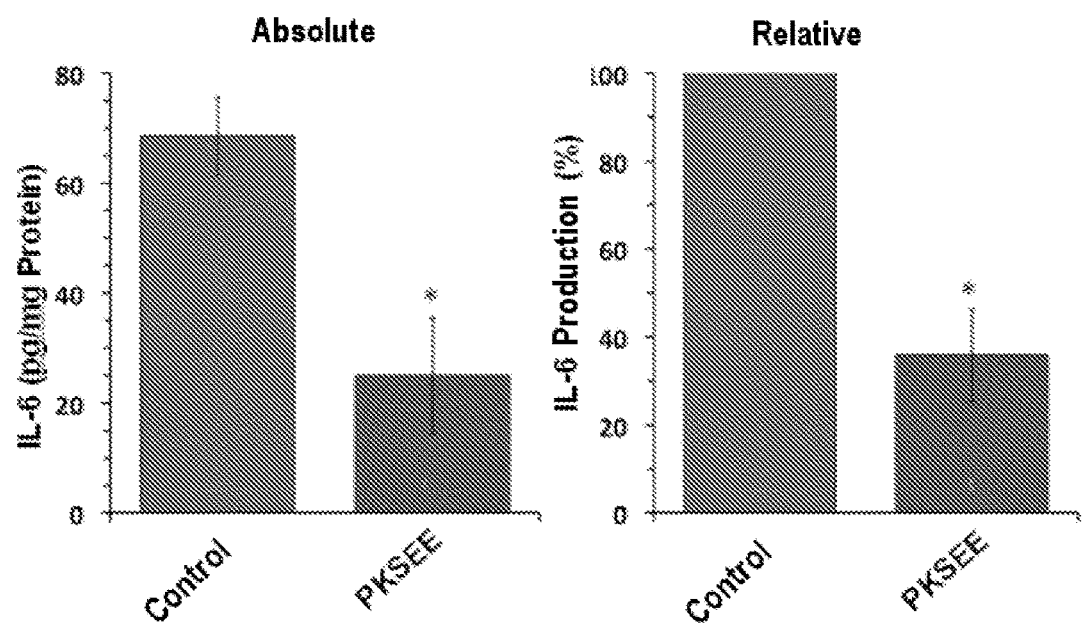

Another test was carried out similarly, the only difference being that the keratinocytes were active at the beginning for 24 hours by adding IL-1β [500 units/ml]. Then, by washing several times, the exogenously added IL-1β was removed from the cultures and the cultures were cultured for a further 24 hours in the normal growth medium. FIG. 2b shows, in comparison with untreated cultures, a marked and significant [Student's t-test] reduction in interleukin-6 synthesis induced by the IL-1β, of the keratinocyte cultures treated with the material according to the invention.

Figure 3A:
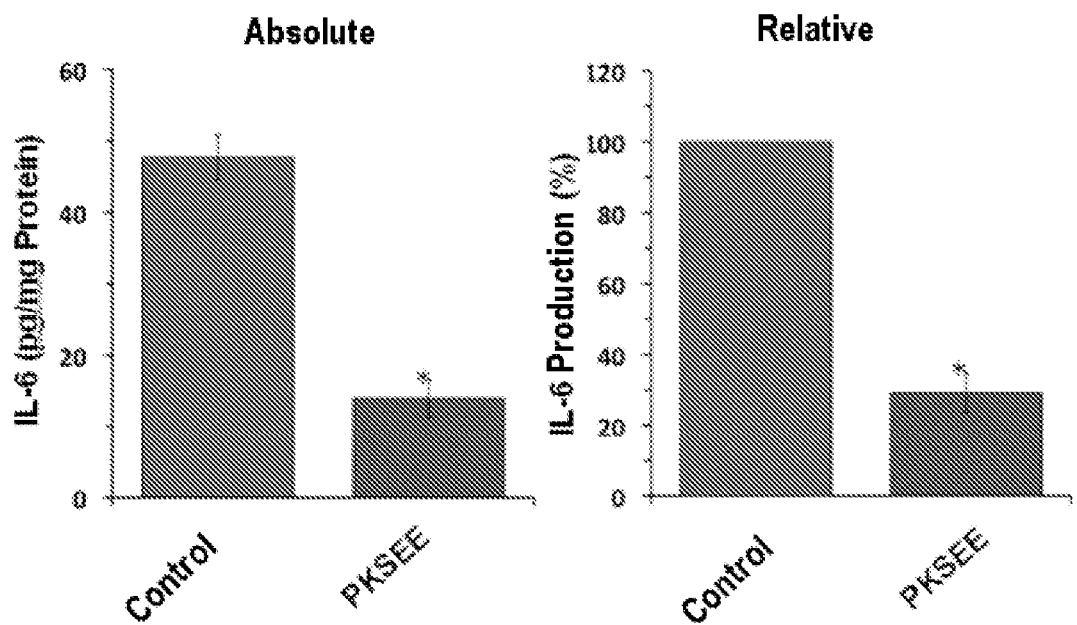
Figure 3B:
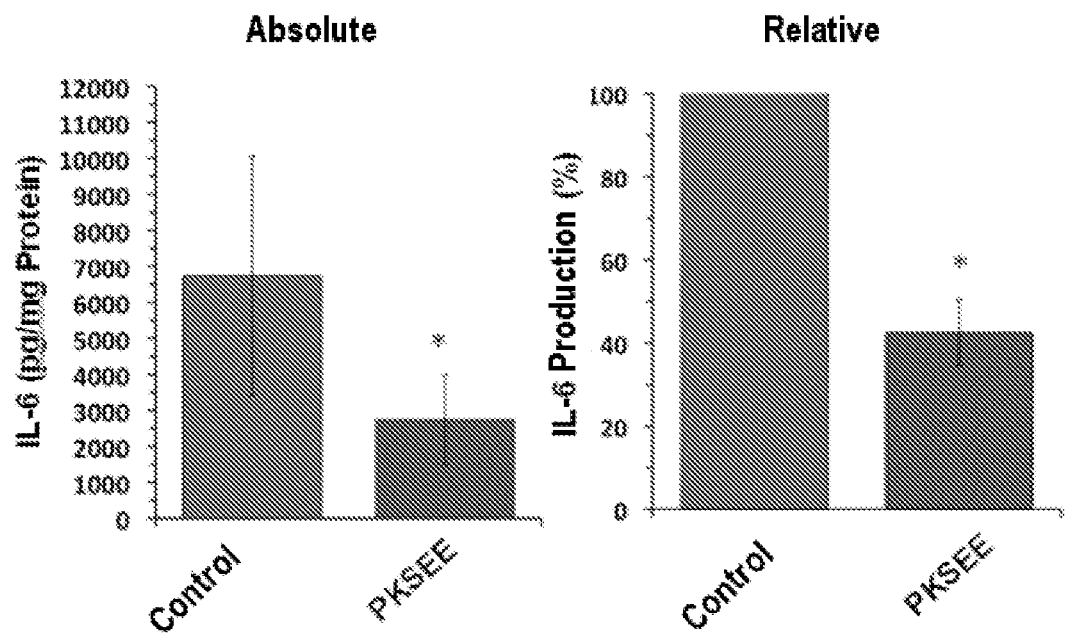
Figure 4A:
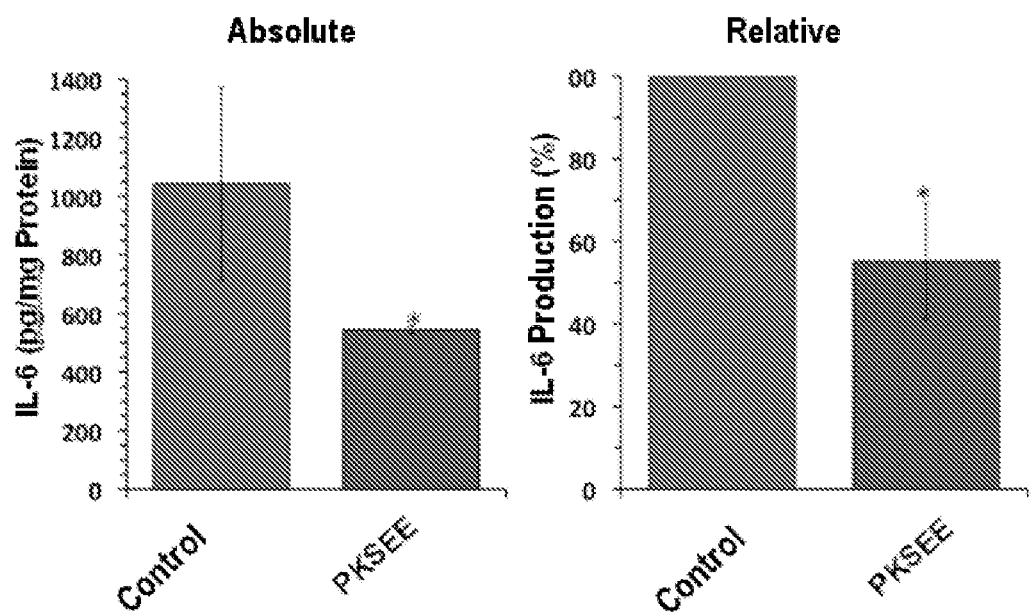
Figure 4B:
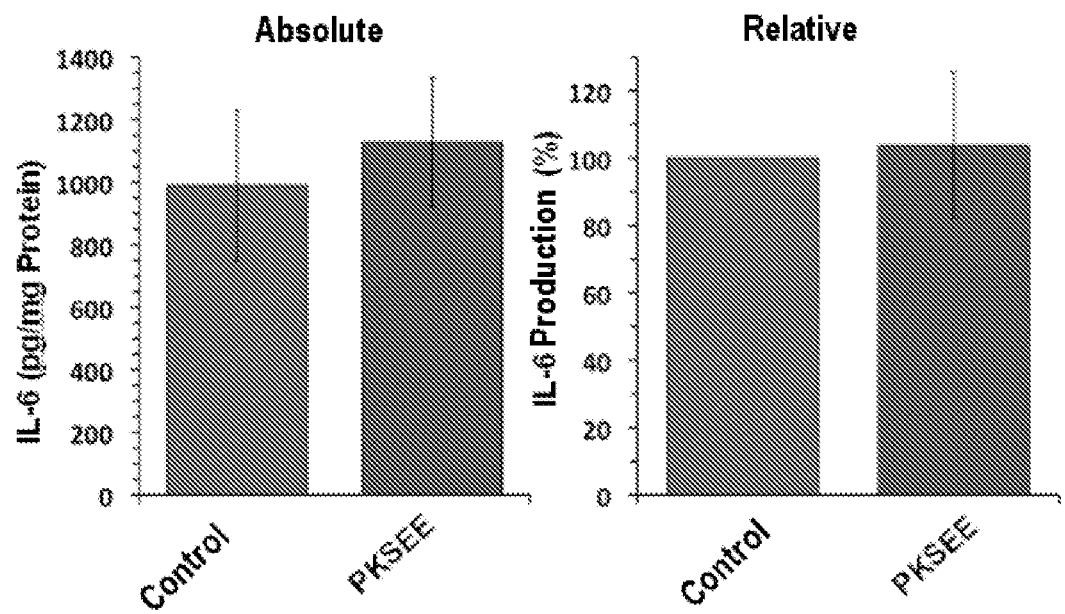

The same tests were carried out for endothelial cells and fibroblasts instead of keratinocytes. FIG. 3a shows a marked and significant [Student's t-test] reduction in constitutive interleukin-6 synthesis in endothelial cells after 72 hours. FIG. 3b shows a marked and significant [Student's t-test] reduction in IL-1β-induced interleukin-6 synthesis in endothelial cells after 72 hours. FIG. 4a shows a marked and significant [Student's t-test] reduction in constitutive interleukin-6 synthesis in fibroblasts after 72 hours. FIG. 4b shows no significant [Student's t-test] reduction in IL-1β-induced interleukin-6 synthesis in fibroblasts.

Figure 5A:
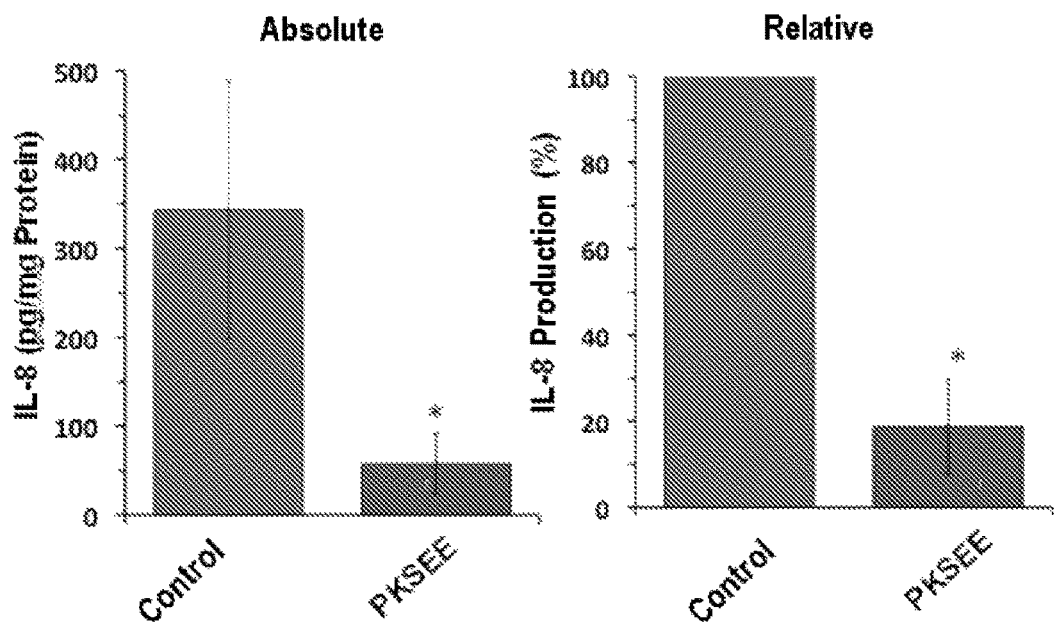
Figure 5B:
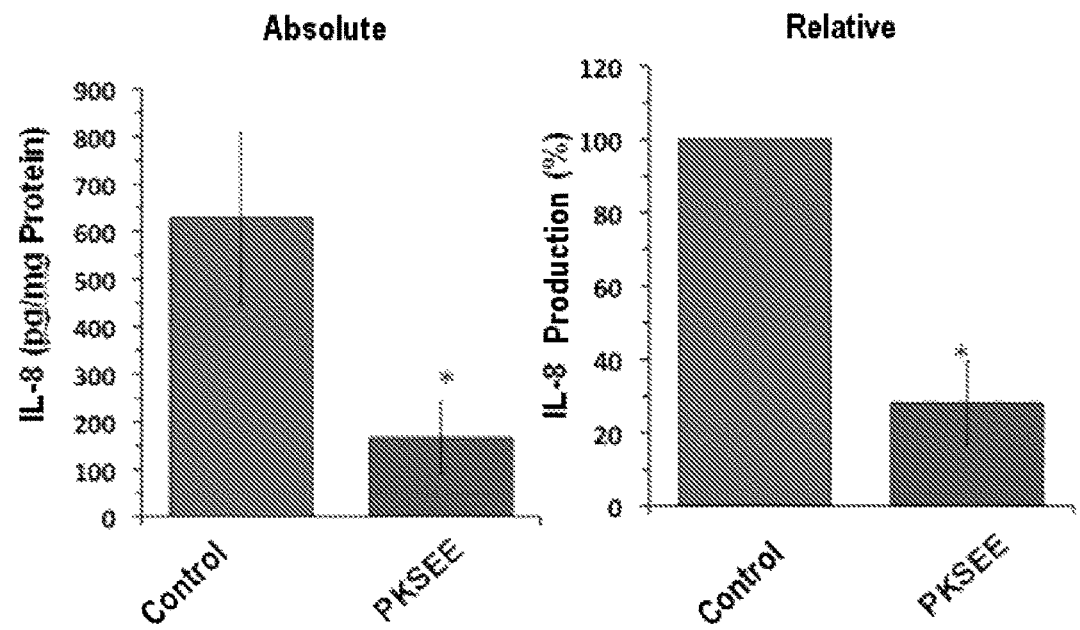

4. Constitutive and Induced Interleukin-8 Synthesis in Keratinocytes, Endothelial Cells and Fibroblasts The same tests as described in Ex. 2 were carried out, except that instead of interleukin-1β, the absolute and relative amount of interleukin-8 in the cell culture supernatants was determined with an ELISA assay [Human IL-8 ELISA kit from R&D Systems]. FIG. 5a shows a marked and significant [Student's t-test] reduction in constitutive interleukin-8 synthesis in keratinocytes after 72 hours. Further tests were carried out similarly, the only difference being that the keratinocytes were activated at the beginning for 24 hours by adding IL-β [500 units/ml]. Then, by washing several times, the exogenously added IL-1β was removed from the cultures, and the cultures were cultured for a further 24 hours in the normal growth medium. FIG. 5b shows, in comparison with untreated cultures, a marked and significant [Student's t-test] reduction in the IL-IP-induced interleukin-8 synthesis of the keratinocyte cultures treated with the material according to the invention.

Figure 6A:
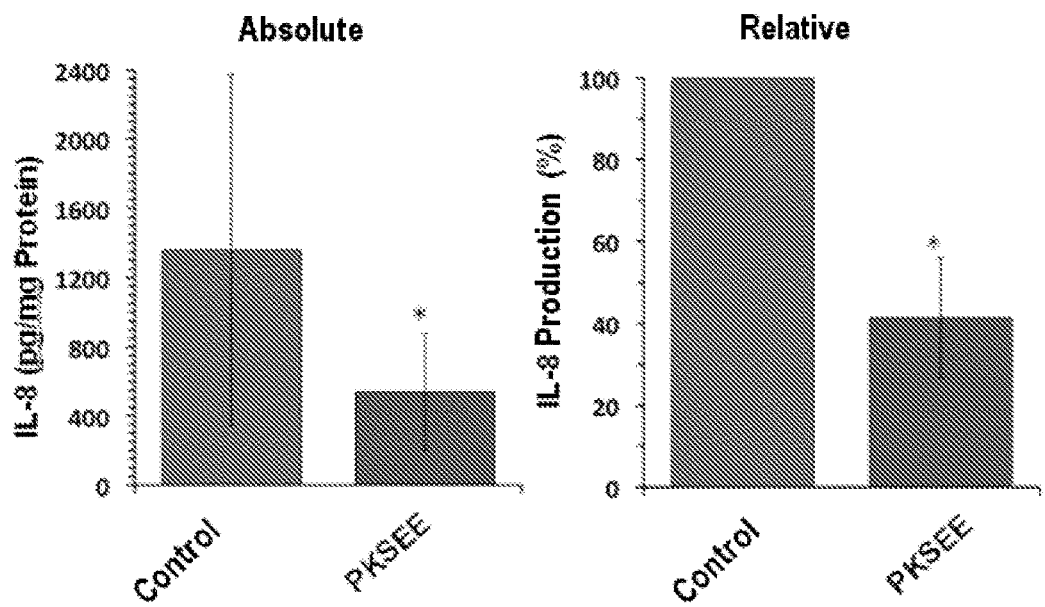
Figure 6B:
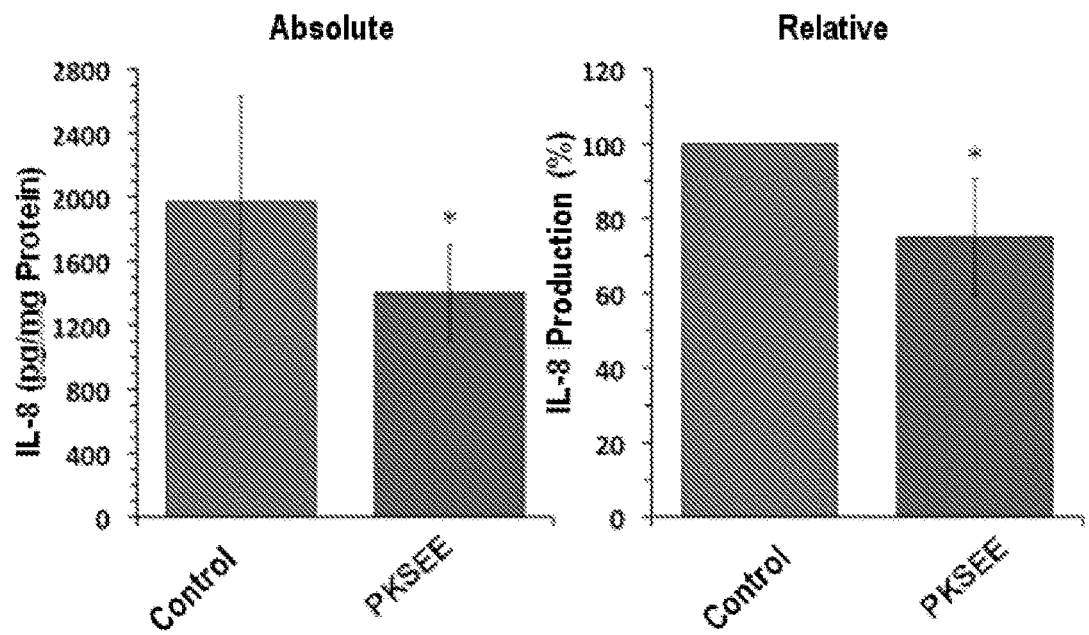
Figure 7A:
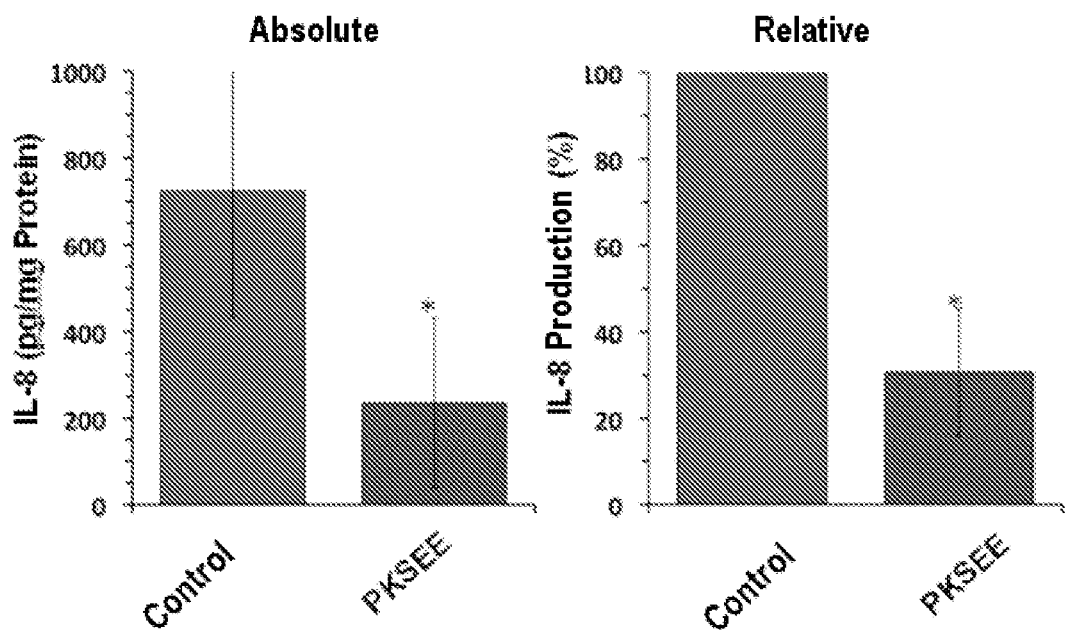
Figure 7B:
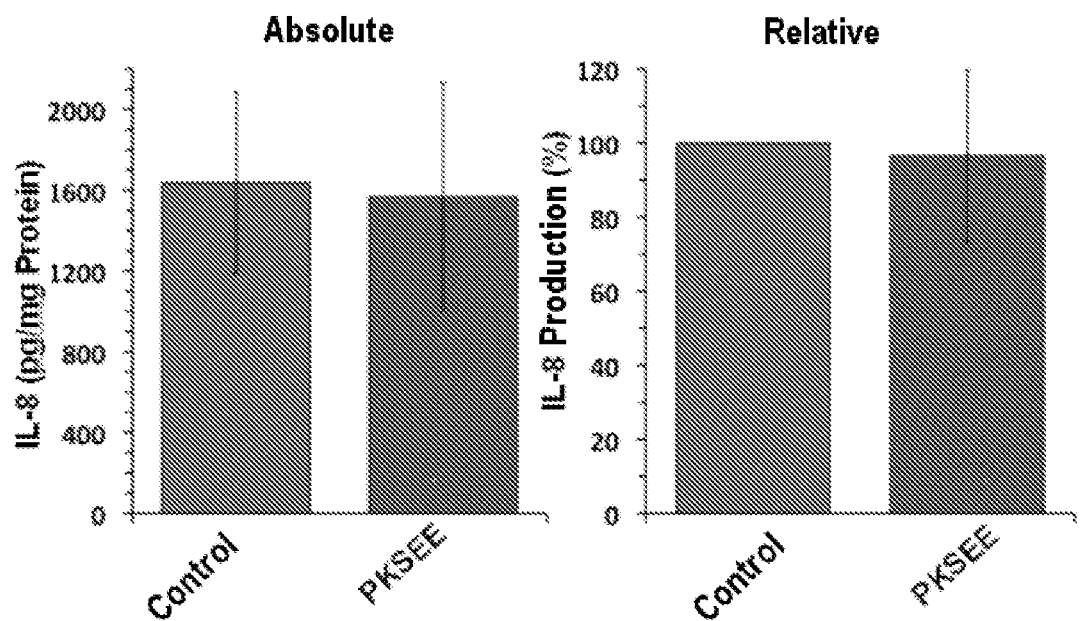

The same tests were carried out with endothelial cells and fibroblasts instead of keratinocytes. FIG. 6a shows a marked and significant reduction in constitutive interleukin-8 synthesis in endothelial cells after 72 hours of culture. FIG. 6b shows a significant [Student's t-test] reduction in induced interleukin-8 synthesis in endothelial cells after 72 hours. FIG. 7a shows a marked and significant [Student's t-test] reduction in constitutive interleukin-8 synthesis in fibroblasts after 72 hours. FIG. 7b shows no significant reduction in induced interleukin 8 synthesis in fibroblasts.

FIGS. 1a, 2a, 3a, 4a, 5a, 6a and 7a: *; p<0.05 compared to the control; n=9; FIGS. 1b, 2b, 3b, 4b, 5b, 6b and 7b: *; p<0.05 compared to the control; n=12; the statistical evaluations were carried out with Student's t-test.

The invention claimed is:

1. A method for preventing and/or treating a disease associated with increased interleukin-1β and/or interleukin-6 and/or interleukin-8 activity and/or disease in which a reduction in the activity of interleukin-1β and/or interleukin-6 and/or interleukin-8 is beneficial for the healing process, said method comprising administering to a subject in need thereof a therapeutically effective amount of a silicon-containing, biodegradable material, wherein the silicon-containing, biodegradable material is a polyhydroxysilicic acid ethyl ester compound, with the proviso that wound defects, comprising chronic diabetic-neuropathic ulcer, chronic leg ulcer, bedsores, secondary-healing infected wounds, non-irritating, primary-healing wounds, ablative lacerations and/or abrasions, are excluded from said disease that can be prevented and/or treated with said material, wherein the polyhydroxysilicic acid ethyl ester compound has a chemical formula $H[OSi_8O_{12}(OH)_x(OC_2H_5)_{6-x}]_n$ OH, wherein x is 2 to 5 and n>1;

wherein said disease is selected from the group consisting of: acute or chronic inflammations of the skin, psoriasis, skin allergies, parasitic skin infection, atopic dermatitis, and pemphigus vulgaris; and wherein the therapeutically effective amount of the silicon-containing-biodegradable material is in total between 0.001 and 100 mg/kg body weight per day and is administered as a single dose or in multiple doses.

2. The method according to claim 1, wherein the material is in the form of a fibre, a fibre matrix, powder, liquid formulation, monolith and/or coating.

3. The method according to claim 2, wherein the silicon-containing, biodegradable material is capable of being produced by:

a) at least one hydrolysis-condensation reaction of tetraethoxysilane b) evaporation for producing a single-phase solution optionally with simultaneous gentle mixing of reaction system;

c) cooling of the single-phase solution;

d) maturation for producing silica sol material; and e) drawing of threads from said silica sol material to generate a fibre or a fibre matrix and/or drying, optionally spray drying or freeze-drying of said silica sol material to generate a powder and optionally dissolving said powder in a solvent to generate a liquid formulation and/or coating said silica sol material on an object that is to be coated with said material, and/or casting said silica sol material in a mould to generate a monolith.

4. The method according to claim 3, wherein the tetraethoxysilane is acid-catalysed in a) at an initial pH from 0 to ≤7, in the presence of a water-soluble solvent, at a temperature from 0° C. to 80° C. and in b), a single-phase solution is evaporated to a viscosity in a range from 0.5 to 2 Pa s at a shear rate of 10 s−1 at 4° C.

5. The method according to claim 4, wherein the acid catalysis in a) is carried out with aqueous solution of nitric acid in a molar ratio to the silicon compound in a range 1:1.7 to 1:1.9.

6. The method of claim 1, wherein said disease is neurodermatitis, dermatomyositis and/or pemphigus vulgaris.

7. The method according to claim 1, wherein the material is in the form of a fibre.

8. The method according to claim 1, wherein the material is in the form of a fibre matrix.

9. The method according to claim 4, wherein the water-soluble solvent is ethanol.

10. The method according to claim 4, wherein the acid catalysis in a) is carried out with aqueous solution of nitric acid in a molar ratio to the silicon compound in a range from 1:1.7 to 1:1.8.

11. The method according to claim 1, wherein the therapeutically effective amount of the silicon-containing-biodegradable material is in total between 0.01 and 25 mg/kg body weight per day and is administered as a single dose or in multiple doses.

12. The method according to claim 1, wherein the therapeutically effective amount of the silicon-containing-biodegradable material is in total between 0.1 and 5 mg/kg body weight per day and is administered as a single dose or in multiple doses.

* * * * *